United States Patent
Xia et al.

(10) Patent No.: US 7,965,388 B2
(45) Date of Patent: Jun. 21, 2011

(54) STRUCTURE FOR SURFACE ENHANCED RAMAN SPECTROSCOPY

(75) Inventors: Qiangfei Xia, Sunnyvale, CA (US); Wei Wu, Palo Alto, CA (US); Zhiyong Li, Redwood City, CA (US); Jing Tang, Sunnyvale, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 178 days.

(21) Appl. No.: 12/416,907

(22) Filed: Apr. 1, 2009

(65) Prior Publication Data

US 2010/0253940 A1    Oct. 7, 2010

(51) Int. Cl.
*G01J 3/44* (2006.01)
*G01N 21/65* (2006.01)

(52) U.S. Cl. ......................... 356/301; 977/712
(58) Field of Classification Search .................. 356/301
See application file for complete search history.

(56) References Cited

U.S. PATENT DOCUMENTS

| 7,307,719 | B2 | 12/2007 | Wang et al. | |
|---|---|---|---|---|
| 7,402,531 | B1 * | 7/2008 | Kuekes et al. | 356/301 |
| 7,483,130 | B2 | 1/2009 | Baumberg et al. | |
| 2006/0038990 | A1 * | 2/2006 | Habib et al. | 356/301 |
| 2006/0274315 | A1 * | 12/2006 | Saito | 356/445 |
| 2007/0177139 | A1 * | 8/2007 | Kamins et al. | 356/301 |
| 2009/0027668 | A1 | 1/2009 | Fujimaki et al. | |

* cited by examiner

*Primary Examiner* — F. L Evans

(57) ABSTRACT

A structure for surface enhanced Raman spectroscopy is disclosed herein. A substrate has a stack configured vertically thereon. The stack encompasses at least two metal layers and at least one dielectric layer therebetween. Each layer of the stack has a controlled thickness, and each of the at least two metal layers is configured to exhibit a predetermined characteristic of plasmonic resonance.

18 Claims, 2 Drawing Sheets

STRUCTURE FOR SURFACE ENHANCED RAMAN SPECTROSCOPY

BACKGROUND

The present disclosure relates generally to structures for use with surface enhanced Raman spectroscopy.

Raman spectroscopy is used to study the transitions between molecular energy states when monochromatic light interacts with molecules, which results in the energy of the light photons being shifted, or scattered. The energy shift provides information of the vibrational energy spacing in the molecular system. Surface enhanced Raman spectroscopy (SERS) enhances Raman scattering via molecules adsorbed on, for example, rough metal surfaces or metal nanoparticle aggregates. The Raman signal enhancement is typically related to the large electric fields generated near the metal surface due to localized surface plasmon resonance. However, the SERS signals strongly depend on the excitation light wavelength. To achieve a large Raman enhancement factor, the excitation light wavelength may be tuned in close proximity to the surface plasmon resonance of the rough metal surfaces or metal nanoparticles.

BRIEF DESCRIPTION OF THE DRAWINGS

Features and advantages of embodiments of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

Embodiments of the structures disclosed herein include vertically oriented nano-antennas or stacks which include at least one dielectric layer sandwiched between metal layers. The vertical orientation of the nano-antenna/stack enables one to control the thickness of the dielectric layer(s) in the stack, and thus the distance between the metal layers in the stack. It is believed that the embodiments of the structures disclosed herein enable systematic control of the plasmonic resonance and plasmonic coupling interaction of the metal layers. Furthermore, each of the stacks may be configured to interact with wavelengths over a broad electromagnetic spectrum (e.g., from near ultraviolet (UV) to near infrared (IR)). Furthermore, in some embodiments, it is believed that different layers within the stacks may advantageously be tuned to provide a multi-resonant nano-antenna/stack. It is believed that this may be accomplished by altering the material of the layer and/or altering the thickness of the dielectric layer(s) in the stack.

Figure 1A:
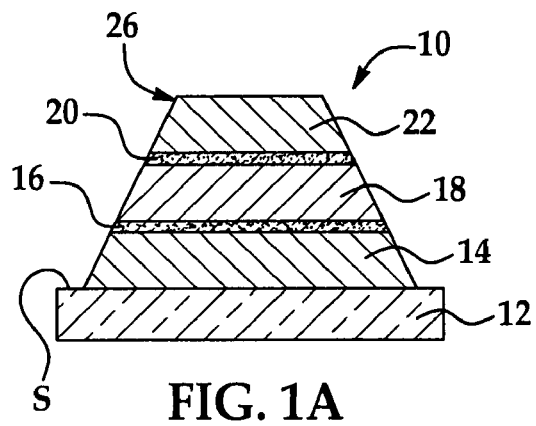
FIG. 1A is a schematic cross-sectional view of an embodiment of a vertical stack.
Figure 1B:
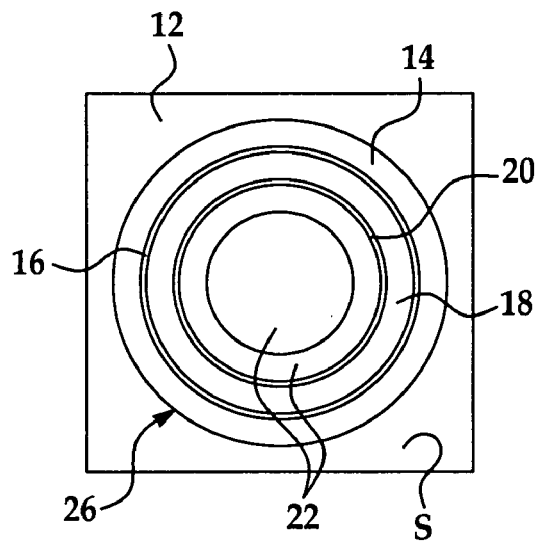
FIG. 1B is a top view of the embodiment of the vertical stack of FIG. 1A.

Referring now to FIGS. 1A and 1B, a cross-sectional view (FIG. 1A) and a top view (FIG. 1B) of an embodiment of a structure 10 is depicted. The structure 10 includes a stack 26 established on a substrate 12. Non-limiting examples of suitable substrate materials include insulators (e.g., glass, quartz, ceramic (alumina), etc.), polymeric material(s) (e.g., polycarbonate, polyamide, acrylics, etc.), or semiconductors (e.g., silicon, InP, GaAs, InAs, $In_xGa_{1-x}As_yP_{1-y}$ (where $0<x<1$, $0<y<1$)), silicon-on-insulator (SOI) substrates, or group III-V semiconductors on silicon on SOI substrates. Other, more flexible polymeric substrates may also be used. In still another embodiment, a waveguide is used as the substrate 12. The use of a waveguide for the substrate 12 provides resonance in addition to the resonance from the stack(s) 26. Furthermore, the waveguide substrate enables the structure 10 to be coupled with a guided mode, thereby achieving uniform SERS enhancement over a large area.

The substrate 12 may be any desirable size. In one embodiment, the substrate 12 may be a wafer having a surface that is at least about 1 $cm^2$. In one embodiment, the substrate 12 wafer has about a 5 mm diameter. In another embodiment, the wafer has a 10 inch diameter or less (e.g., 9 inches, 8 inches, 6.5 inches, 6 inches, 5.75 inches, 4 inches, or any other measurement between 0 and 10 inches). The substrate 12 size may be selected, at least in part, based upon the end application, the lithography capability, the cost involved, etc. As such, the example sizes given herein are for illustrative purposes, and it is to be understood that any desirable substrate size may be utilized. It is believed that larger substrates 12 are particularly suitable for the method(s) disclosed hereinbelow for manufacturing a plurality of the stack(s) 26.

The stack 26 includes alternating layers 14, 16, 18, 20, 22 of metal and dielectric materials. Since the layers 14, 16, 18, 20, 22 are stacked one on top of the other on top of the substrate 12, the stack 26 extends vertically out of the plane of the substrate surface S. It is to be understood that any number of metal layers 14, 18, 22 and dielectric layers 16, 20 may be utilized, as long as one of the metal layers 14 is established directly on the substrate 12, another of the metal layers 22 is the outermost layer of the stack 26, and dielectric layer(s) 16, 20 separate adjacent metal layers 14, 18, 22. In one non-limiting example, the stack 26 includes two metal layers 14, 18 with dielectric layer 16 established therebetween. In the non-limiting example shown in FIGS. 1A and 1B, the stack 26 includes three metal layers 14, 18, 22 with dielectric layers 16, 20 established therebetween. It is to be understood that any desirable number of layers 14, 16, 18, 20, 22 may be included in the stack 26.

The metal layers 14, 18, 22 may be formed of gold, silver, copper, aluminum, or alloys thereof. It is to be understood that the metal layers 14, 18, 22 may all be formed of the same material, may all be formed of different materials, or one or more may be formed of one material while other(s) are formed of another material.

The dielectric layer(s) 16, 20 may be selected from any dielectric material such as glass, insulating polymers (e.g., poly(vinylphenol) (PVP), poly(methyl methacrylate) (PMMA), polycarbonate, silicone, polyimide, etc.), oxides (e.g., silicon dioxide, aluminum oxide (alumina), zirconium oxide, hafnium oxide, titanium oxide, etc.), nitrides (e.g., silicon nitride ($Si_3N_4$)), or combinations thereof.

The metal layers 14, 18, 22 and the dielectric layer(s) 16, 20 may be sequentially established on the substrate surface S. A material suitable for forming the metal layer 14 is deposited and patterned on the substrate surface S to achieve a desirable shape and thickness $t_{14}$. A material suitable for forming the dielectric layer 16 is then deposited and patterned on the metal layer 14 to achieve a desirable shape and thickness $t_{16}$. A material suitable for forming the metal layer 18 is then deposited and patterned on the dielectric layer 16 to achieve a desirable shape and thickness $t_{18}$. It is to be understood that each subsequent dielectric layer 20 and metal layer 22 is patterned and deposited until the final metal layer (in this example layer 22) is established. The layers 14, 16, 18, 20, 22 may be patterned via a lithography technique, including, but not limited to, nanoimprint lithography, photolithography, focused ion beam lithography, and combinations thereof, and may be deposited via electron beam evaporation, thermal evaporation, sputtering, chemical vapor deposition (CVD), or atomic layer deposition (ALD). It is to be understood that the layers 14, 16, 18, 20, 22 may each be patterned and/or deposited via the same technique, or via different techniques.

As mentioned above, each layer 14, 16, 18, 20, 22 is established to have a desirable shape. In one non-limiting example, the shape of each layer 14, 16, 18, 20, 22 is a disc shape (i.e., round and has a diameter). A stack 26 in which each of the layers 14, 16, 18, 20, 22 is formed in the disc shape is shown in FIGS. 1A and 1B. It is to be understood that the size of the disc shaped layers 14, 16, 18, 20, 22 may be the same or different. In the examples of FIGS. 1A and 1B, the top or outermost layer 22 is the smallest in diameter, and each underlying layer 16, 18, 20, 22 increases in diameter. Also in this example, the edge of each layer 14, 16, 18, 20, 22 is tapered, and thus the diameter of each layer 14, 16, 18, 20, 22 is continuously varied along the respective thickness $t_{14}$, $t_{16}$, $t_{18}$, $t_{20}$, $t_{22}$ of each of the layers 14, 16, 18, 20, 22. Furthermore, as shown in FIGS. 1A and 1B, the varying diameter of each layer 14, 16, 18, 20, 22 may be different from the varying diameter of each other layer 14, 16, 18, 20, 22. In other embodiments, the edges may not be tapered. In these other embodiments, while the diameter of each layer 14, 16, 18, 20, 22 may be different from the diameter of each other layer 14, 16, 18, 20, 22, the respective diameters of the layers 14, 16, 18, 20, 22 may be consistent throughout the respective thicknesses $t_{14}$, $t_{16}$, $t_{18}$, $t_{20}$, $t_{22}$.

Shapes other than the previously mentioned disc shape may be suitable for the layers 14, 16, 18, 20, 22. In fact, any regular or irregular shape may be utilized. Other non-limiting examples of such shapes include squares, rectangles, triangles, etc. The desirable shape may be obtained, for example, by using an imprint mold configured to transfer the desirable shape (e.g., during nanoimprint lithography), using a mask configured to transfer the desirable shape (e.g., during photolithography), and/or altering the deposition or other processing conditions.

During patterning and/or deposition of the respective layers 14, 16, 18, 20, 22, the processing conditions may be modified to control the thickness $t_{14}$, $t_{16}$, $t_{18}$, $t_{20}$, $t_{22}$ of the resulting layers 14, 16, 18, 20, 22. Generally, the thicknesses $t_{14}$, $t_{16}$, $t_{18}$, $t_{20}$, $t_{22}$ may each be controlled by the deposition time, rate, etc. The thickness $t_{14}$, $t_{18}$, $t_{22}$ of each of the metal layers 14, 18, 22 is controlled such it generally ranges from about 5 nm to about 200 nm. The thickness $t_{14}$, $t_{18}$, $t_{22}$ of each of the metal layers 14, 18, 22 may be the same or different.

The thickness $t_{16}$, $t_{20}$ Of the dielectric layer(s) 16, 20 is controlled such that adjacent metal layers 14, 18 and 18, 22 are separated by a desirable distance (i.e., the dielectric layer (s) 16, 20 create a "gap" between adjacent metal layers 14, 18 and 18, 22). This desirable distance (or dielectric material gap) is small enough such that the adjacent metal layers 14, 18 and 18, 22 experience plasmonic coupling interactions. It is believed that stronger plasmonic coupling interactions provide an enhanced field for the generation of the SERS signals. Such coupling interactions result when the thickness $t_{16}$, $t_{20}$ of the dielectric layer(s) 16, 20 ranges from about 1 nm to about 20 nm. As such, the thicknesses $t_{16}$, $t_{20}$ may be altered such that each metal layer 14, 18, 22 provides a predetermined characteristic of plasmonic resonance. The metal selected for the layers 14, 18, 22 also contributes to the plasmonic resonance achieved. As such, the metal material and dielectric layer thicknesses $t_{16}$, $t_{20}$ may be controlled in order to achieve the desirable plasmonic resonance.

The typical plasmonic resonance of silver is about 350 nm and gold is about 500 nm. When the layers 14, 18, 22 include metal nanoparticles, the resonance can be red-shifted (i.e., longer wavelengths). As a non-limiting example, silver nanoparticles having diameters of about 40 nm are utilized to form the layers 14, 18, 22, and the thickness of the dielectric layers 16, 20 ranges from about 0 nm to about 40 nm or more. The corresponding plasmon frequencies in this non-limiting example are as follows: at 0 nm dielectric layer 16, 20 thicknesses, the plasmon resonance of the layers 14, 18, 22 ranges from 700 nm to 800 nm; at 10 nm dielectric layer 16, 20 thicknesses, the plasmon resonance of the layers 14, 18, 22 ranges from 500 nm to 600 nm; at 20 nm dielectric layer 16, 20 thicknesses, the plasmon resonance of the layers 14, 18, 22 is about 500 nm; and at dielectric layer 16, 20 thicknesses of 30 nm or more, the plasmon resonance of the layers 14, 18, 22 ranges from 400 nm to 500 nm.

Figure 2:
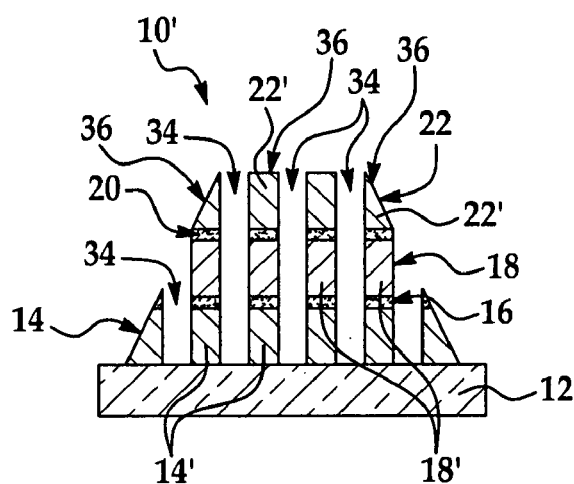
FIG. 2 is a schematic cross-sectional view of another embodiment of a vertical stack including substructures formed in each of the layers.
Figure 3:
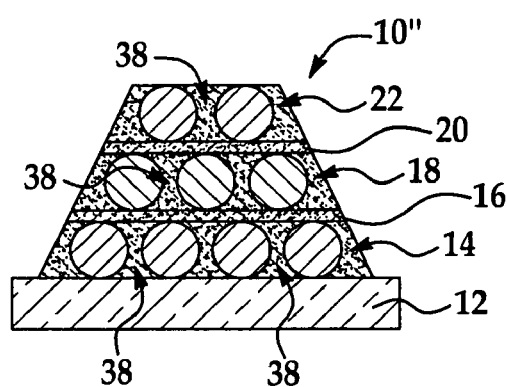
FIG. 3 is a schematic cross-sectional view of an embodiment of a vertical stack including discontinuous metal layers.

FIGS. 2 and 3 depict other embodiments of the structure 10', 10'' that may be formed via the method(s) disclosed herein. It is to be understood that the various configurations (e.g., shapes) and materials described above for each of the layers 14, 16, 18, 20, 22 may be used in such embodiments.

Specifically referring now to FIG. 2, another embodiment of the structure 10' is depicted. In this embodiment, each metal layer 14, 18, 22 includes discontinuous islands 14', 18', 22' of the metal materials, each of which has a portion of the dielectric layers 16, 20 therebetween. These stacked islands 14', 18', 22' and dielectric layers 16, 20 form a plurality of sub-structures 36 having spaces 34 therebetween. In an embodiment, the spacing between the sub-structures 36 (i.e., the width of the spaces 34) ranges from about 1 nm to about 100 nm, or from about 5 nm to about 100 nm. The width of the spaces 34 may be selected such that the analytes (in either liquid or gas form) to be tested have suitable access to the sub-structures 36 via the spaces 34. Such access may be particularly desirable because the edges of the sub-structures 36 may have the largest electromagnetic enhancement of the structure 10'. In this embodiment of the structure 10', the width/diameter of the sub-structures 36 (i.e., the stacked islands 14', 18', 22' with dielectric layers 16, 20 therebetween) ranges from about 20 nm to about 100 nm, and in some instances, is up to about 1000 nm.

Specifically referring now to FIG. 3, still another embodiment of the structure 10'' is depicted. In this embodiment, each metal layer 14, 18, 22 is discontinuous as a result of being very thin (i.e., thinner than a critical thickness to form a continuous film), or of being deposited on a surface having low surface energy (i.e., any surface upon which the deposited material will de-wet (e.g., a TEFLON® (from E.I. Du Pont de Nemours and Co., Delaware) coated surface)). Such discontinuous films/layers include spaces or pores 38 formed within/between the deposited metal. When discontinuous metal layers 14, 16, 18 are formed, it is to be understood that the material(s) used to form the dielectric layers 16, 20 may be deposited into the spaces/pores 38. Generally, the dielectric material between the spaces/pores 38 results from the deposition of the layers 16, 20. In a non-limiting example of this embodiment of the structure 10", a silver or gold metal layer 14, 18, 22 having a thickness less than 10 nm is a discontinuous film on a silicon oxide surface.

Figure 4:
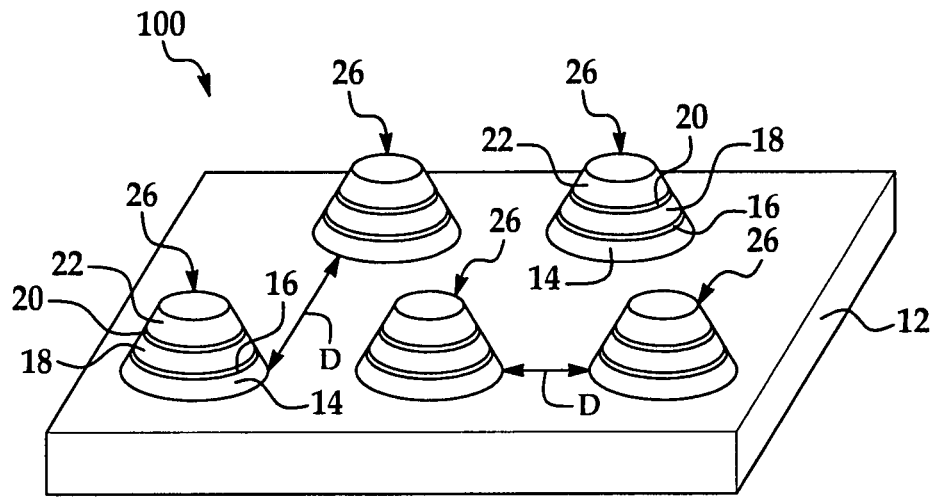
FIG. 4 is a schematic perspective view of an embodiment of a structure including a plurality of vertical stacks.

Referring now to FIG. 4, a plurality of stacks 26 is distributed on the substrate 12 to form an array 100. The stacks 26 are formed of materials and via methods described in reference to FIGS. 1A and 1B.

The stacks 26 in the array 100 may be distributed in a periodic fashion such that each stack 26 is a predetermined distance from an adjacent stack 26. The distances D between each of the stacks 26 may be equivalent or different. As an example, the stacks 26 in one row may be separated from each other by first distances D, and the stacks 26 in the second row may be separated by second, larger distances D. In an embodiment, the distance D between adjacent stacks 26 generally ranges from about 10 nm to about 10 μm. The distance D is controlled during lithography. For example, in nanoimprint lithography, the distance D is controlled by the mold used, and in photolithography, the distance D is controlled by the photomask used.

The structures 10, 10', 10" and array 100 disclosed herein are suitable for use in standard Raman detection procedures. Generally, analyte molecules are distributed on the stack(s) 26, and are subsequently subjected to laser excitation of suitable wavelengths. The resulting signals are detected using known detectors.

Figure 5:
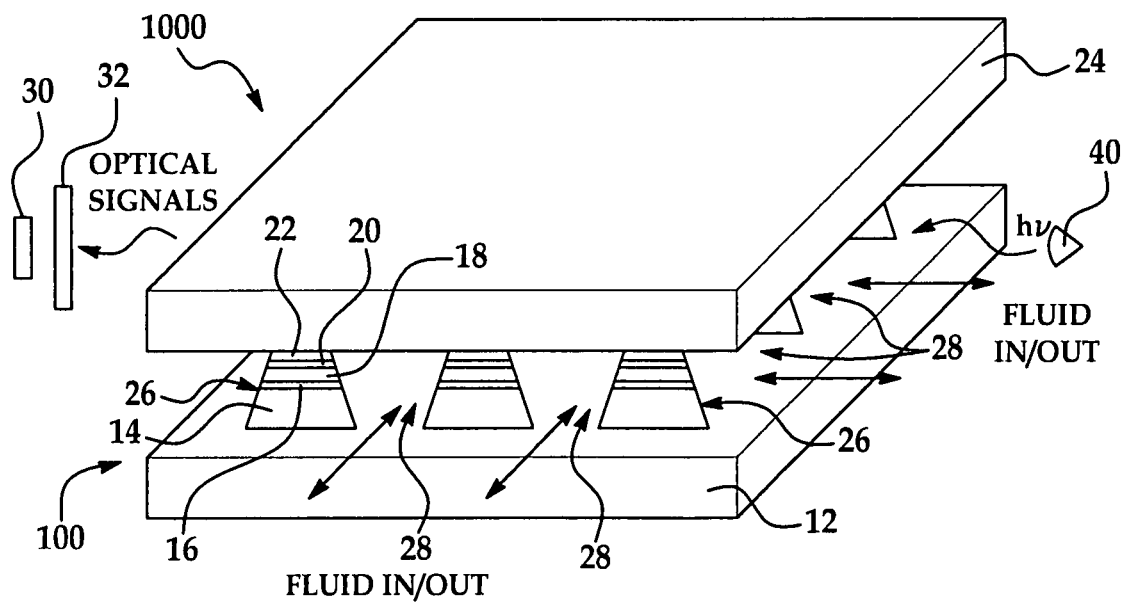
FIG. 5 is a schematic perspective view of an embodiment of a structure including transparent cover plate on the plurality of vertical stacks.

Referring now to FIG. 5, in still another embodiment, the array 100 is incorporated into an optofluidic device 1000. To generate such a device 1000, the array 100 is formed (by forming stacks 26 on the substrate 12 using methods described hereinabove), and a transparent cover plate 24 (i.e., that is at least transparent to the desirable wavelengths of light used during sensing) is secured to the outer most layers 22 of the stacks 26. The cover plate 24 may be secured using techniques, such as wafer bonding, or transfer printing (i.e., reversal imprint). The transparent cover plate 24 may be formed of glass, transparent polymers, quartz, or other like materials. When the cover plate 24 is established on the array 100, fluidic channels 28 are formed between the substrate 12 and the cover plate 24 and between adjacent stacks 26.

Fluid containing one or more analytes or species of interest may be directed through the channels 28 such that they interact with the stacks 26 and light directed thereon to generate one or more signals. The fluid (i.e., a gas or liquid) may be directed through the channels 28 actively or passively. In one embodiment, positive pressure may be applied through an inlet of or more of the channels 28 to push the fluid into the device 1000, negative pressure may be drawn from one or more outlets of the channels 28 to pull the fluid out of the device 1000, or both positive and negative pressure may be used to direct the fluid in a desirable direction through the channels 28.

The fluid flow may be restricted at the ends of the channels 28 by operatively positioning, at one or more of the ends, a stopping mechanism (not shown) that is transparent to the desirable wavelength transmitted through the device 1000 and to the optical signal that is generated. Examples of such stopping mechanisms include glass, silicon dioxide, or suitable polymers.

The species within the channels 28 will interact with the stack(s) 26 and the light directed therein from light source 40 (e.g., lasers or light emitting diodes), and such interaction generates optical signals that are detectable via suitable detectors 30. The interaction of light with the species may be identified via a shift in the energy of the light photons. The detected optical signals may then be used to identify the species or analyte.

In any of the embodiments disclosed herein, waveguides (not shown) may be used to direct the light into and out of the device 1000. Furthermore, in any of the embodiments disclosed herein, one or more filters 32 (shown in FIG. 5) may be positioned between the area of the device 1000 at which the optical signals exit the device 1000 and the corresponding detector 30. Such filters 32 may be used to selectively allow optical signals of one or more desirable wavelengths to pass through to the detector 30 while rejecting optical signals of one or more other wavelengths. One non-limiting example of such a filter 32 is a grating based optical filter.

The embodiments of the structure 10, 10', 10" and array 100 disclosed herein may advantageously be used in a variety of applications, including SERS and optofluidics. The individual layers 14, 16, 18, 20, and 22 within the vertically oriented stack 26, and thus the vertically oriented stack 26 itself, may be tuned to achieve desirable plasmonic resonance (s). As such, a single band or multi-band structure 10, 10', 10" may advantageously be generated.

While several embodiments have been described in detail, it will be apparent to those skilled in the art that the disclosed embodiments may be modified. Therefore, the foregoing description is to be considered exemplary rather than limiting.

What is claimed is:

1. A structure for surface enhanced Raman spectroscopy, comprising:
    a substrate; and
    a stack configured vertically on the substrate, the stack including at least two metal layers and at least one dielectric layer therebetween, each layer of the stack having a controlled thickness, and each of the at least two metal layers configured to exhibit a predetermined characteristic of plasmonic resonance;
    wherein each layer in the stack has the same shape, and wherein a size of the shape of each layer is different from a size of the shape of each of the other layers.

2. The structure as defined in claim 1 wherein the stack further includes an other dielectric layer established on an outermost of the at least two metal layers, and an other metal layer established on the other dielectric layer.

3. The structure as defined in claim 1 wherein one of the at least two metal layers in the stack is formed of a first metal, wherein an other of the at least two metal layers in the stack is formed of a second metal, and wherein the first and second metals are different.

4. The structure as defined in claim 1 wherein the controlled thickness of the at least one dielectric layer ranges from about 1 nm to about 20 nm.

5. The structure as defined in claim 4 wherein the controlled thickness of the at least one dielectric layer is selected such that the metal layers adjacent thereto are configured to generate plasmonic coupling for improved field enhancement.

6. The structure as defined in claim 1 wherein the controlled thickness of each of the at least two metal layers ranges from about 5 nm to about 200 nm.

7. The structure as defined in claim 1 wherein the substrate is a waveguide.

8. A structure for surface enhanced Raman spectroscopy, comprising:
    a substrate;
    a plurality of stacks, each of which is configured vertically on the substrate, each stack including at least two metal layers and at least one dielectric layer therebetween, each layer of each stack having a controlled thickness, and each of the at least two metal layers of each stack configured to exhibit a predetermined characteristic of plasmonic resonance, wherein each of the plurality of stacks is separated from an adjacent stack by a predetermined distance; and a transparent cover plate contacting each of the plurality of stacks such that fluidic channels are defined between the substrate and the transparent cover plate and between the plurality of stacks.

9. A structure for surface enhanced Raman spectroscopy, comprising:
   a substrate; and
   a stack configured vertically on the substrate, the stack including at least two metal layers and at least one dielectric layer therebetween, each layer of the stack having a controlled thickness, and each of the at least two metal layers configured to exhibit a predetermined characteristic of plasmonic resonance;
   wherein each layer in the stack has a disc shape, and wherein a diameter of each layer is different from a diameter of each of the other layers.

10. The structure as defined in claim 9 wherein the respective diameters continuously vary along the respective thickness of each of the layers in the stack.

11. The structure as defined in claim 9 wherein the diameter of an outermost layer of the stack is the smallest of the diameters, and wherein the diameter of an innermost layer of the stack is the largest of the diameters.

12. A structure for surface enhanced Raman spectroscopy, comprising:
   a substrate;
   a stack configured vertically on the substrate, the stack including at least two metal layers and at least one dielectric layer therebetween, each layer of the stack having a controlled thickness, and each of the at least two metal layers configured to exhibit a predetermined characteristic of plasmonic resonance; and
   spaces positioned such that the at least two metal layers and the at least one dielectric layer are configured as a plurality of sub-structures including discontinuous islands of metal and dielectric materials.

13. The structure as defined in claim 12 wherein each space is filled with air and provides access for at least one analyte to contact an adjacent one of the plurality of sub-structures.

14. A method for making the structure as defined in claim 1, the method comprising:
   establishing a first of the at least two metal layers on the substrate;
   establishing the dielectric layer on the first metal layer;
   establishing a second of the at least two metal layers on the dielectric layer; and
   controlling each of the establishing steps such that each of the established layers has a respective predetermined thickness;
   wherein the establishing steps are accomplished such that each layer has the predetermined shape and such that the size of the predetermined shape of each layer is different from the size of the predetermined shape of each of the other layers.

15. The method as defined in claim 14 wherein establishing is at least partially accomplished via a lithography technique selected from the group consisting of nanoimprint lithography, photolithography, focused ion beam lithography, and combinations thereof.

16. The method as defined in claim 14 wherein establishing is at least partially accomplished via electron beam evaporation, thermal evaporation, sputtering, chemical vapor deposition, or atomic layer deposition.

17. The method as defined in claim 14 wherein the predetermined thickness of the dielectric layer is selected such that the first and second metal layers are configured to have plasmonic coupling interactions.

18. A system incorporating the structure as defined in claim 8, the system comprising:
   a light source positioned at an input of at least one of the fluidic channels and configured to direct light into the at least one of the fluidic channels;
   a detector positioned at an output of at least one of the fluidic channels and configured to detect at least one optical signal exiting the at least one of the fluidic channels; and
   a filter positioned at the output of at least one of the fluidic channels and configured to selectively enable the at least one optical signal to pass through to the detector while rejecting other optical signals.

* * * * *